United States Patent [19]

King

[11] Patent Number: 5,253,658
[45] Date of Patent: Oct. 19, 1993

[54] PATIENT MOUTHPIECE DEVICE WITH CONTAMINATION SHIELD

[75] Inventor: Russell W. King, Sierra Madre, Calif.

[73] Assignee: Medi-Nuclean Corporation, Inc., Baldwin Park, Calif.

[21] Appl. No.: 881,064

[22] Filed: May 11, 1992

[51] Int. Cl.⁵ .............................................. A61C 5/14
[52] U.S. Cl. .................................................. 128/859
[58] Field of Search ........................ 128/859–861, 128/200.14; 2/2

[56] References Cited

U.S. PATENT DOCUMENTS

| | | | |
|---|---|---|---|
| 2,589,504 | 3/1952 | Miller | 128/861 |
| 3,107,667 | 10/1963 | Moore | 128/861 |
| 3,123,069 | 3/1964 | Laisne | 128/865 |
| 3,139,088 | 6/1964 | Galleher | 128/859 |
| 4,270,531 | 6/1981 | Blachly | 128/861 |
| 4,275,725 | 6/1981 | Nelson | 128/859 |
| 4,907,581 | 3/1990 | King | 128/200.14 |
| 4,928,710 | 5/1990 | Campbell | 128/861 |
| 4,944,313 | 7/1990 | Katz | 128/859 |
| 5,074,375 | 12/1991 | Grozil | 128/864 |

*Primary Examiner*—Michael A. Brown
*Attorney, Agent, or Firm*—Brunton, J. E.

[57] ABSTRACT

A patient mouthpiece apparatus which incorporates a removable covering, or protective shield, for maintaining cleanliness of the mouthpiece prior to patient use, and for containment of saliva or other body fluids which might be on or in the mouthpiece or associated breathing tube after patient use, thereby preventing possible contamination spread.

16 Claims, 1 Drawing Sheet

PATIENT MOUTHPIECE DEVICE WITH CONTAMINATION SHIELD

BACKGROUND OF THE INVENTION

1. Field of the Invention

The present invention relates generally to instrumentation used in the areas of inhalation therapy, respiratory therapy or respiratory diagnostic procedures in the field of medicine. More particularly, the invention concerns a patient mouthpiece device incorporating a protective covering, or enclosure, for encapsulating the patient mouthpiece section both before and after use to prevent spread of contamination.

2. Discussion of the Prior Art

Inhalation therapy and respiratory diagnostic procedures as they relate to patient care have been well documented and have been accepted standard practices in hospitals, extended care facilities, and even private homes for many years. Daily, numerous patient procedures are routinely practiced in such facilities which require that the patient breathe from, through or into some special respiratory system or equipment. In most instances, the interface between patient and instrumentation involves a patient mouthpiece and a length of flexible corrugated tubing. Characteristically, as the patient breathes back and forth through the mouthpiece and tubing, varying amounts of saliva become entrapped in the mouthpiece and corrugated tubing. Upon removal of the mouthpiece from the patient, the saliva immediately becomes a source of cross-contamination for anything or anyone that might come in contact with it. Often substantial amounts of saliva are present in the mouthpiece and its associated tubing and will leak out unless the technologist takes extra precaution and wraps the mouthpiece in some type of absorbent material.

This situation creates not only an unsanitary condition for the technologist, but also creates extremely hazardous possibilities of contamination spread. Where the procedure involves radioactive materials, the hazardous spread of radiation contamination is also quite possible.

Another source of cross-contamination in respiratory areas results from the procedure for attaching the new mouthpiece to the associated instrumentation. Typically, the mouthpiece is removed from its container by the technologist and one end thereof is inserted into either a length of breathing tubing or into a bacterial filter. Commercially produced prior art patient mouthpieces are generally no more than two and one-half inches in length, and approximately one-third of this length must be pushed into the cooperating tubing or filter. In so doing, it is almost impossible for the technologist to properly attach the mouthpiece without handling and severely risking contaminating the mouthinsertion end of the device.

As will be appreciated from the discussion which follows, the present invention for the first time addresses and uniquely solves the problems set forth in the preceding paragraphs.

SUMMARY OF THE INVENTION

It is an object of the present invention to provide a patient mouthpiece apparatus which incorporates a cover or shield, that, when fitted over and around the patient mouthpiece will entrap any saliva contained therein and will effectively prevent external leakage of possibly highly contaminated saliva.

Another object of the invention is to provide a device of the aforementioned character which will also serve as a cover to protect the mouthpiece from handling and possible contamination by the technologist prior to patient use and during interconnection with the mouthpiece with the associated supply tubing or equipment.

A further object of the invention is to provide a patient mouthpiece apparatus which incorporates a fitted removable protective shield that will fully encapsulate that area of the mouthpiece which has been in contact with the patient's mouth to prevent technologist contact with the contaminated area.

Yet another object of the invention is to provide a patient mouthpiece apparatus which incorporates a fitted removable protective shield of the character described that can be quickly and easily attached to the patient mouthpiece without the operator having to touch any contaminated area.

Still another object of the invention is to provide a patient mouthpiece apparatus incorporating a fitted removable protective shield as herein described which is simple in design, easy to use and inexpensive to manufacture in large volume.

DESCRIPTION OF THE INVENTION

Figure 1:
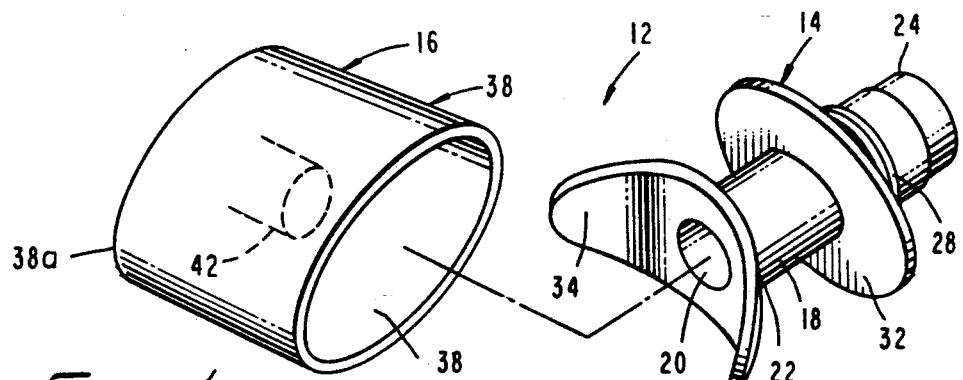
FIG. 1 is an exploded, generally perspective view of the patient mouthpiece apparatus of one form of the invention.
Figure 2:
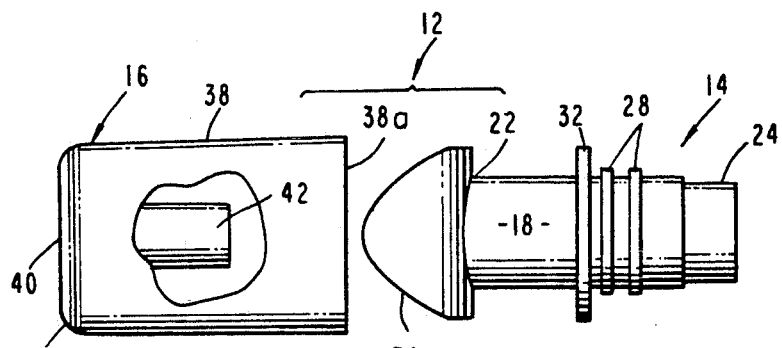
FIG. 2 is an exploded, side elevational view of the apparatus partly broken away to show internal construction.
Figure 3:
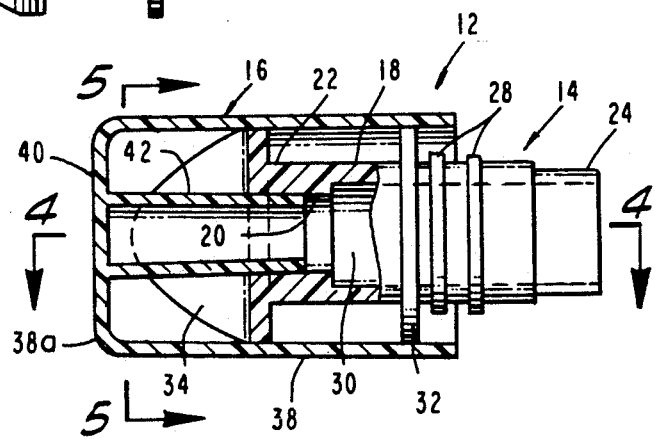
FIG. 3 is a side elevational, cross-sectional view of the apparatus showing the protective cover in position over the mouthpiece portion of the device.

Referring to the drawings and particularly to FIGS. 1, 2 and 3, the patient mouthpiece apparatus of the form of the invention there illustrated is generally designated by the numeral 12. This embodiment apparatus of the invention is adapted for use in connection with respiratory equipment for supplying fluids such as liquids and gases to a patient through a conduit which interconnects the remotely located respiratory equipment with the mouthpiece portion of the apparatus.

As best seen by referring to FIG. 1, the apparatus comprises a first, or mouthpiece portion, 14 and a second, or mouthpiece encapsulation, portion 16. The mouthpiece portion includes a generally tubular shaped body 18 having an elliptical shaped fluid passageway 20 therethrough. Body 18 has first and second ends generally designated as 22 and 24. Second end 24 is adapted to be interconnected with the remotely located respiratory equipment and connector means are provided for that purpose. In the present embodiment of the invention, the connector means comprises a pair of longitudinally spaced, radially outwardly extending ribs 28 which circumscribe body 18. When the conduit which interconnects the mouthpiece with the remotely located respiratory equipment comprises a yieldably deformable plastic tube the open end of the plastic tube is closely receivable over and held in place by ribs 28. The conduit may also comprise a filter unit in which case the inlet of the filter unit is receivable over and held in place by ribs 28. Disposed within the central portion of body 18 is an internal saliva entrapment cavity generally designated by the numeral 30.

Referring particularly to FIGS. 1 and 3, it is to be noted that a first generally planar wall 32 circumscribes body 18 at a location intermediate the first and second ends thereof. Planar wall 32 is generally elliptical in shape and, as will presently be described, is closely receivable within the open end of the skirt portion of the encapsulating means of this form of the invention.

A second, generally elliptically shaped curved wall 34 is located proximate the first end of body 18. Wall 34 is specially configured to be comfortably received within the patient's mouth.

The novel shape of wall 34 uniquely permits the mouthpiece portion 14 to be held comfortably and securely in place within the patient's mouth during the introduction of fluids from the remotely located respiratory equipment. While various other configurations of wall 34 can be used, the generally elliptical shape shown in FIG. 1 of the drawings has proven to be quite successful in clinical tests.

Figure 4:
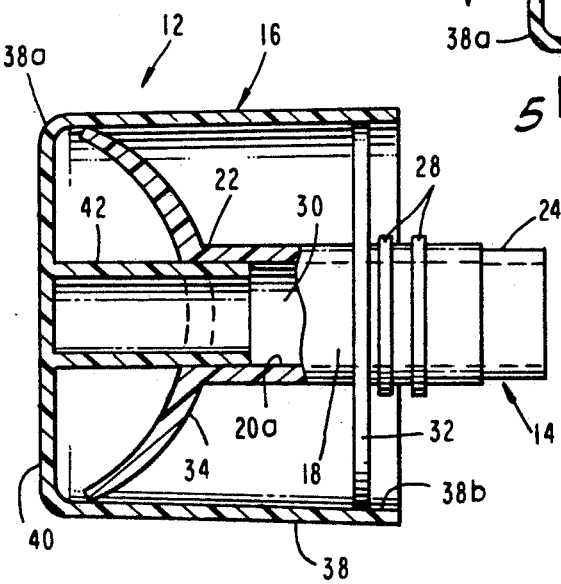
FIG. 4 is a top, cross-sectional view taken along lines 4—4 of FIG. 3.
Figure 5:
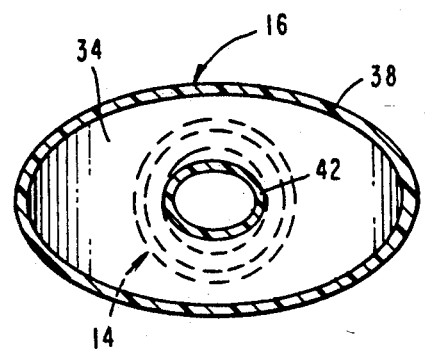
FIG. 5 is a cross-sectional view taken along lines 5—5 of FIG. 3.

The second, or mouthpiece encapsulation, portion, of the apparatus comprises a hollow skirt portion 38 which is closely receivable over walls 32 and 34 of mouthpiece portion 14. As best seen by referring to FIG. 3, skirt portion 38 has a first end 38a which is sealably closed by an integrally formed end closure wall 40. The open end 38b of the skirt 38 is configured so as to closely and sealably receive wall 32 of the mouthpiece portion in the manner shown in FIGS. 3 and 4. In FIG. 5, the cross-section of the skirt portion is elliptical shaped. In this regard, it is to be noted that skirt portion 38 tapers slightly outwardly from wall 40 so that as the mouthpiece portion 14 is inserted into the encapsulation portion, wall 32 will tightly engage the internal wall of skirt 38 at a location slightly inboard of the open end 38b. With this construction, the mouthpiece portion 14 will be secureably sealed within, and encapsulated by, the encapsulation portion 16.

Another important feature of the apparatus of the invention comprises the sealing means of the device for sealably closing the fluid passageway 20 of body 18. In the present embodiment of the invention the sealing means comprises an inwardly tapering closure member 42 which has a cross-section that is elliptical shape end is integrally formed with, and extends inwardly of, wall 40 in the manner shown in FIGS. 3, 4, and 5. Closure member 42 is closely receivable within passageway 20 of body 18 and, due to its inwardly tapering configuration, will sealably engage the inner wall 20a of passageway 20 so as to positively seal off the saliva entrapment chamber 30 and effectively prevent any leakage of saliva from the device.

The apparatus of the invention can be constructed of a variety of materials. However, in practice both the first and second portions of the device are integrally formed of a moldable plastic material such as polyethylene or polypropylene.

In using the apparatus of the present invention to safely seal off a possibly contaminated mouthpiece relative to atmosphere, encapsulating portion 16 is placed over mouthpiece portion 14 while portion 14 is still connected to the respiratory equipment. Because the patient has breathed inwardly and outwardly through the mouthpiece, varying amounts of saliva have become entrapped in the cavity portion 30 and within the passageway 20 of the mouthpiece portion. As the encapsulating portion is placed over and urged into engagement with the mouthpiece portion, the sealing means or closure member 42 will be closely received within passageway 20 so as to sealably close the passageway and isolate the saliva entrapment chamber from atmosphere. At the same time that the closure member 42 is being forced into sealing engagement with the inner wall of passageway 20, closure wall 32 of the mouthpiece is being moved into sealable engagement with the inner wall of the skirt portion 38. The fit of the closure member 42 to passageway 20 and of wall 32 to skirt 38 is such that frictional forces will securely hold together the first and second portion of the apparatus. In this matted position, the interior of the mouthpiece containing the patient's saliva is effectively sealed relative to atmosphere. Further, since the encapsulating means of the apparatus completely encapsulates that portion of the mouthpiece section which has been in the patient's mouth, spread of contamination from the surfaces which have been in contact with the patient's mouth is also effectively prevented.

Another important aspect of the apparatus of the present invention resides in its pretreatment during interconnection of the mouthpiece portion with the auxiliary respiratory equipment, such as a piece of breathing tube, bacterial filter or the like. So long as the protective shield or encapsulating portion is in position around the mouthpiece section, the apparatus can be safely handled by the technologist without fear of contaminating the mouthpiece. More particularly, end 24 of the mouthpiece can be interconnected with the conduit or bacterial filter, which forms a part of the remotely located respiratory equipment, without fear of contamination of those surfaces of the mouthpiece which are to be received within the patient's mouth. This unique feature of the apparatus effectively prevents the spread of contamination from the technologist to the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A patient mouthpiece for use in connection with respiratory equipment of the character used in supplying fluids to a patient, comprising:
    (a) a first portion including:
        (i) an elongated body having a fluid passageway therethrough, said body having a first end and a second end for interconnection with the respiratory equipment;
        (ii) a first wall circumscribing said body at a location intermediate said first and second ends;
        (iii) a second wall being curved and receivable within the patient's mouth, said second wall circumscribing said body proximate said first end thereof whereby said first portion can be securely supported in place during the supply of fluids to the patient;
    (b) a second portion for removable interconnection with said first portion, comprising a skirt portion receivable over said second curved wall of said first portion, said skirt portion being closed at one end by a closure wall and having an opening at the opposite end for closely receiving said first wall of said first portion, said second portion further, including sealing means for sealably closing said fluid passageway of said body of said first portion.

2. A patient mouthpiece as defined in claim 1 in which said sealing means comprises a sealing member extending inwardly from said closure wall of said second portion, said closure member being closely receivable within said fluid passageway of said body of said first portion when said first and second portions are connected together.

3. A patient mouthpiece as defined in claim 1 in which said elongated body is provided with an internal saliva trapping cavity.

4. A patient mouthpiece as defined in claim 1 further including connector means provided on said elongated body for interconnecting said first portion with the respiratory equipment.

5. A patient mouthpiece as defined in claim 4 in which said connector means comprise a pair of longitudinally spaced ribs circumscribing said body intermediate said first wall and said second end of said body.

6. A patient mouthpiece as defined in claim 4 in which said skirt of said second portion is generally elliptical in cross section.

7. A patient mouthpiece as defined in claim 6 in which said skirt of said second portion tapers outwardly from said one end to said opposite end.

8. A patient mouthpiece as defined in claim 6 in which said fluid passageway of said body is generally elliptical in cross-section.

9. A patient mouthpiece apparatus for use in connection with respiratory equipment of the character used in supplying fluids such as liquids and gases to a patient through a conduit which is interconnected with remotely located respiratory equipment, said mouthpiece apparatus comprising:
   (a) a mouthpiece portion, including:
      (i) a tubular body having a fluid passageway therethrough, said body having a first end and a second end for interconnection with the conduit of the respiratory equipment, said tubular body having an internal saliva entrapment cavity;
      (ii) a first generally planar wall circumscribing said tubular body and located intermediate said first and second ends thereof;
      (iii) a second wall being curved and generally elliptically shaped, circumscribing said tubular body and located proximate said first end thereof, said second wall being receivable within the patient's mouth so as to securely support said mouthpiece portion in place during the supply of fluids to the patient;
   (b) a mouthpiece encapsulation portion for removable interconnection with said first portion, comprising:
      (i) a hollow skirt portion receivable over said second curved wall of said mouthpiece portion, said skirt portion having a first end and a second end adapted to closely receive said first wall of said mouthpiece portion;
      (ii) an end closure wall connected to said first end of said skirt portion;
      (iii) a closure member connected to said end closure wall and extending inwardly into said hollow skirt portion, said closure member being sealably receivable within said fluid passageway of said body of said mouthpiece portion.

10. A patient mouthpiece apparatus as defined in claim 9 in which said closure member tapers inwardly from said end closure wall toward said second end of said hollow skirt portion.

11. A patient mouthpiece apparatus as defined in claim 10 in which said tubular body of said mouthpiece portion includes connector means for interconnecting said mouthpiece portion with the conduit leading to the remotely located respiratory equipment.

12. A patient mouthpiece apparatus as defined in claim 11 in which said connector means comprises a pair of spaced-apart ribs circumscribing said body and extending radially outwardly therefrom.

13. A patient mouthpiece apparatus as defined in claim 11 in which said hollow skirt portion is generally elliptical in cross-section.

14. A patient mouthpiece apparatus for use in connection with respiratory equipment of the character used in supplying fluids such as liquids and gases to a patient through a conduit which is interconnected with remotely located respiratory equipment, said mouthpiece apparatus comprising:
   (a) a mouthpiece portion, including:
      (i) a tubular body having a fluid passageway therethrough, said body having a first end and a second end provided with a pair of spaced-apart, circumscribing ribs for interconnection with the conduit of the respiratory equipment, said tubular body also having an internal saliva entrapment cavity;
      (ii) a first generally planar wall circumscribing said tubular body and located intermediate said first and second ends thereof;
      (iii) a second wall being curved and generally elliptically shaped, circumscribing said tubular body and located proximate said first end thereof, said second wall being receivable in the patient's mouth to securely support said mouthpiece portion in place during the supply of fluid to the patient;
   (b) a mouthpiece encapsulation portion for removable interconnection with said first portion, comprising:
      (i) a hallow skirt portion receivable over said second curved wall of said mouthpiece portion, said skirt portion having a first end and a second end adapted to closely receive said first wall of said mouthpiece portion;
      (ii) an end closure wall connected to said first end of said skirt portion;
      (iii) an inwardly tapering closure member connected to said end closure wall and extending inwardly into said hallow skirt portion, said closure member being sealably receivable within said fluid passageway of said body of said mouthpiece portion.

15. A patient mouthpiece as defined in claim 14 in which said hollow skirt portion is generally elliptical in cross-section.

16. A patient mouthpiece as defined in claim 14 in which said hallow skirt portion includes a wall tapering outwardly from said first end to said second end.

* * * * *